US012649014B2

(12) United States Patent　　　(10) Patent No.:　US 12,649,014 B2
Cho et al.　　　　　　　　　　　　(45) Date of Patent:　　　Jun. 9, 2026

(54) DECONTAMINANT GENERATING SYSTEM

(71) Applicant: AGENCY FOR DEFENSE DEVELOPMENT, Daejeon (KR)

(72) Inventors: Kyeong Min Cho, Daejeon (KR); Heesoo Jung, Daejeon (KR); Sang Myeon Lee, Daejeon (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 19/048,051

(22) Filed: Feb. 7, 2025

(65) Prior Publication Data

US 2026/0077081 A1　　Mar. 19, 2026

(30) Foreign Application Priority Data

Sep. 13, 2024　　(KR) ......................... 10-2024-0125522

(51) Int. Cl.
　　A61L 9/12　　　　　(2006.01)
(52) U.S. Cl.
　　CPC ............. A61L 9/12 (2013.01); A61L 2202/15 (2013.01)
(58) Field of Classification Search
　　CPC ................................................ A61L 2202/122
　　See application file for complete search history.

(56) References Cited

U.S. PATENT DOCUMENTS

| | | | |
|---|---|---|---|
| 6,982,006 B1 * | 1/2006 | Boyers .............. | H01L 21/31133 |
| | | | 134/28 |
| 2017/0202877 A1 * | 7/2017 | Hoover .................. | A61K 8/891 |
| 2021/0038439 A1 * | 2/2021 | Torii ................. | A61F 13/15617 |

FOREIGN PATENT DOCUMENTS

| | | | | | |
|---|---|---|---|---|---|
| DE | 102018008666 A1 | * | 5/2020 | .............. | A61L 2/18 |
| JP | 2002544504 A | * | 12/2002 | ............. | A61L 2/186 |
| KR | 20090112364 A | * | 10/2009 | ....... | A61L 2202/122 |
| KR | 1020110128393 | | 11/2011 | | |
| KR | 1020210099697 | | 8/2021 | | |
| KR | 102500811 B1 | * | 2/2023 | ....... | A61L 2202/122 |
| WO | WO-2016064288 A1 | * | 4/2016 | ............. | A61L 2/202 |
| WO | WO-2019084203 A1 | * | 5/2019 | ........... | A61L 2/0082 |

(Continued)

OTHER PUBLICATIONS

JP_2002544504_A_translation (Year: 2002).*

(Continued)

*Primary Examiner* — Kevin Joyner
*Assistant Examiner* — Changru Chen
(74) *Attorney, Agent, or Firm* — Riverside Law LLP

(57)　　　　　　ABSTRACT

Provided is a decontaminant generating system including an active species generation unit configured to generate an active species for decontamination, a gas-liquid mixing unit configured to form reaction activated water by dissolving the active species for decontamination generated from the active species generation unit in an aqueous solution, a decontaminant mixing unit configured to form a decontaminant by mixing the reaction activated water formed in the gas-liquid mixing unit with a decontamination composition in a granular form, a powder form, or both forms, a storage configured to store the decontaminant formed in the decontaminant mixing unit, a spraying unit configured to spray the decontaminant stored in the storage, and an integrated control unit configured to control operating variables and perform monitoring in real time.

1 Claim, 5 Drawing Sheets

(56)                    References Cited

FOREIGN PATENT DOCUMENTS

WO      WO-2021257460 A1 * 12/2021    ............. A61L 2/183

OTHER PUBLICATIONS

KR_102500811_B1_translation (Year: 2023).*
KR_20090112364_A_translation (Year: 2009).*
Cho, K. M., "Future Wide-Area Decontamination and On-Site Production of Decontaminants," Korean Society of Chemical, Biological and Radiological Defense Fall 2023, Sep. 22, 2023, 14 Pages.
Cho, K. M., et al., "On-site Production of Decontaminnat and Decon-Station," Korean Institute of Military Science and Technology—2024 General Conference: Chemical, Biological, Radiologial, and Environmental Sector, Jun. 13, 2024, 4 Pages.

* cited by examiner

DECONTAMINANT GENERATING SYSTEM

CROSS-REFERENCE TO RELATED APPLICATION

This application claims the benefit of Korean Patent Application No. 10-2024-0125522 filed on Sep. 13, 2024, in the Korean Intellectual Property Office, the entire disclosure of which is incorporated herein by reference for all purposes.

BACKGROUND

1. Field of the Invention

One or more embodiments relate to a decontaminant generating system for generating a decontaminant containing an active species for decontamination using air or water in an atmosphere without an external gas supply.

2. Description of the Related Art

In the past, people were constantly threatened by the possibility of terrorism or war, such as biological weapons and chemical weapons such as anthrax, blister agents, and nerve agents. In particular, chemical and biological weapons require low cost and may be spread without distinction between civilians and soldiers, and thus the damage may be enormous. Unlike traditionally distinguished biological and chemical weapons, new viruses such as COVID-19 and new chemical agents such as Novichok are making humanity more anxious in recent times. In addition, it is very important to develop decontaminants for effective response to the emergence of new viruses and new chemical weapons. However, there are various decomposition mechanisms for agents for pollutants, it is inconvenient to respond with an appropriate decontaminant. When a decontamination target has a wide area, there is a risk of not having enough decontaminant to decontaminate the target, and a risk of missing an appropriate decontamination time, which may lead to the continued spread of contamination that is not blocked in a timely manner.

In particular, a chlorine-based decontaminant currently in use is highly corrosive and not environmentally friendly, and therefore, there is a high possibility that serious secondary problems will arise when conducting decontamination operations in urban areas. Research has been conducted overseas to solve this problem by using oxygen-based decontaminants, and a hydrogen peroxide-based decontaminant is being used. Hydrogen peroxide is manufactured using a thermochemical industrial hydrogen peroxide production technology. An anthraquinone (AQ) process used for mass production of hydrogen peroxide includes a reduction (hydrogenation) step, an oxidation step, and an extraction step under AQ and organic solvents. In the reduction step, an expensive precious metal (Pd) catalyst and a hydrogen gas (~4 bar, 50° C.) are required, and in the extraction step, a separate complicated separation process (an organic solvent, a reaction product, and the like) is required, and therefore, there are limitations in on-site production.

In order to remove contamination in a timely manner and block its spread through rapid and continuous decontamination operations, it is very important to secure a technology for manufacturing a decontaminant in real time.

In this regard, a method of minimizing byproducts after decontamination by utilizing water, air, and electricity is emerging as the safest and most environmental-friendly method. First, methods of utilizing electricity for decontamination include plasma, electrolysis, photochemical production, high-energy beams, nanocatalyst process technology, and the like.

In particular, when a high voltage is applied to two electrodes at a certain interval, a discharge is formed in a space between the electrodes, ionization of a reaction gas occurs, and plasma is formed. The plasma formed in this way contains numerous functional ions, electrons, and active species, and is effectively used for surface cleaning of materials, removal of fine foreign substances, change in surface roughness, formation of polar functional groups, generation of chemical species, and the like.

As a technology for producing active species and hydrogen peroxide using plasma, first of all, a technology for producing oxygen active species and hydrogen peroxide through plasma DBD discharge and a reaction with water in a microreactor is reported. Various oxygen and nitrogen active species may be generated through water, air, and energy, but there is currently a limitation that a concentration of active species generated is low.

In addition, a technology for producing high-purity hydrogen peroxide through plasma reaction of hydrogen and oxygen is reported. The technology may produce hydrogen peroxide with a very high concentration, but it requires hydrogen, and therefore, the suitability of on-site production technology must be considered.

Next, a technology for producing an electrochemical chemical product may be considered. Research is actively being conducted to produce chemical products such as hydrogen peroxide and hypochlorous acid by electrochemically reacting with water, air, and electrolytes. Both hydrogen peroxide and hypochlorous acid are strong oxidizing agents and they may be determined as being usable for reactive decontamination.

In particular, with the development of nanocatalysts (electrocatalysts), research is being reported on environmentally friendly production of hydrogen peroxide through electrochemical reactions of water and oxygen, and up to 1-2% levels are achieved on a laboratory scale. However, the technological maturity is immature in terms of semi-permanent electrolyte development and electrode stability, as well as system design for mass production.

As a technology for producing photochemical hydrogen peroxide, research for generating electrons using light energy under a photocatalyst and producing oxygen-based radical and hydrogen peroxide by reacting with other chemicals such as water and the like is being reported. Compared to other technologies, it has the advantage of simple equipment and operating principles, but the technology for producing hydrogen peroxide with a high concentration and in large quantities has not yet been developed, and additional processes for recovering catalysts and the like are required.

In addition, as other methods, in addition to ozone generation using plasma, there is a technology for producing hydrogen peroxide through an ozonolysis reaction. It is a technology for producing gaseous hydrogen peroxide from ozone through the ozonolysis reaction of unsaturated fatty acid, and is a technology for converting ozone generated through plasma and a light source into hydrogen peroxide. However, the yield is very low so far, and a mass production process design is required.

Recently, research is being conducted to produce decontaminants in real time using various methods as described above. However, there is a limit to producing a decontaminant with a high concentration by using the above methods alone, and thus, there is a need for a new system for producing a decontaminant with a high concentration.

The above description has been possessed or acquired by the inventor(s) in the course of conceiving the present disclosure and is not necessarily an art publicly known before the present application is filed.

SUMMARY

Embodiments provide a decontaminant generating system for generating a decontaminant containing an active species for decontamination using air or water in an atmosphere without an external gas supply.

Also, embodiments provide a decontaminant generating system capable of quickly and safely performing decontamination and sterilization at the right time by generating a high-concentration decontaminant in real time to overcome various shortcomings of the decontamination/sterilization system currently used for civilian medical purposes or the military.

However, technical goals to be achieved are not limited to those described above, and other goals not mentioned above may be clearly understood by one of ordinary skill in the art from the following description.

According to an aspect, there is provided a decontaminant generating system including an active species generation unit configured to generate an active species for decontamination, a gas-liquid mixing unit configured to form reaction activated water by dissolving the active species for decontamination generated from the active species generation unit in an aqueous solution, a decontaminant mixing unit configured to form a decontaminant by mixing the reaction activated water formed in the gas-liquid mixing unit with a decontamination composition in a granular form, a powder form, or both forms, a storage configured to store the decontaminant formed in the decontaminant mixing unit, a spraying unit configured to spray the decontaminant stored in the storage, and an integrated control unit configured to control operating variables and perform monitoring in real time.

The active species for decontamination may include at least one selected from the group consisting of an active nitrogen species, an active oxygen species, and effective chlorine, the active nitrogen species may include at least one selected from the group consisting of $NO_3^-$, $NO_2^-$, and $ONOO^-$, the active oxygen species may include at least one selected from the group consisting of $H_2O_2$, $O_3$, and $OH^-$, and the effective chlorine may include $Ca(ClO)_2$, $NaClO$, and $HClO^-$.

The active species generation unit may be configured to receive external air without additional supply of an external discharge gas, and generate the active species for decontamination through discharge of atmospheric pressure plasma by applying a frequency of 10 kHz to 2.45 GHz to the supplied external air.

The active species generation unit may include at least one selected from the group consisting of a plasma discharge module, an electrolysis module, a photochemical production module, a high energy beam, and a nano-catalyst module.

The active species for decontamination having a concentration of 1 wt % to 10 wt % may be generated by the active species generation unit.

The active species for decontamination may be generated by the active species generation unit at a production speed of 10 L/h to 1,000 L/h.

The gas-liquid mixing unit may include a packed column, a module type membrane contactor, or both.

The gas-liquid mixing unit may be configured to dissolve 99% or more of a high-concentration gas.

The decontamination composition in a granular form, a powder form, or both forms may provide a decontamination reaction tailored to a decontamination target, and the decontamination composition in a granular form, a powder form, or both forms may include at least one selected from the group consisting of a commercial decontaminant, a chlorine-based decontaminant, and an oxygen-based decontaminant.

The storage may be configured to store the active species for decontamination for 7 to 30 days.

The integrated control unit may be configured to integrally control the active species for decontamination to control a concentration and a production speed of the active species for decontamination.

The decontaminant generating system may further include a water purification unit, a cooling unit, or both.

The water purification unit may be configured to control a contamination level of a water source obtained from the group consisting of tap water, river water, and sea water to an electrical conductivity of 1 mS/cm or less.

The cooling unit may be configured to cool the decontaminant to a temperature range of 10° C. to 40° C.

The decontaminant may decontaminate/sterilize chemical weapons and biological weapons that have penetrated 10 mm or more into a surface of a nonporous medium and a porous medium.

Additional aspects of embodiments will be set forth in part in the description which follows and, in part, will be apparent from the description, or may be learned by practice of the disclosure.

The type of active species for decontamination of the decontaminant may be controlled through the decontaminant generating system according to an embodiment of the present disclosure. In addition, the decontaminant may be generated in real time when a concentration, a generated amount, activity, and a production speed of the decontaminant are controlled. Also, the discharge of atmospheric pressure plasma is possible without additional supply of an external discharge gas. In addition, a decontamination reaction tailored to a decontamination target may be provided by mixing the decontaminant generated through the decontaminant generating system with a commercial decontaminant.

Chemical weapons (chemical agents) and biological weapons (biological agents) in a nonporous medium may be decontaminated/sterilized through the decontaminant generating system according to an embodiment of the present disclosure.

The decontaminant generating system according to an embodiment of the present disclosure may be applied to various decontamination and sterilization technologies including material property changes, surface modification, material synthesis, and cleaning in an environmental purification technology, a medical and bio-industry technology, an energy and material industry, a processing industry, and a weapon system.

However, the effects of the present invention are not limited to those described above and may be expanded in various manners within the scope without departing from the spirit and field of the disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
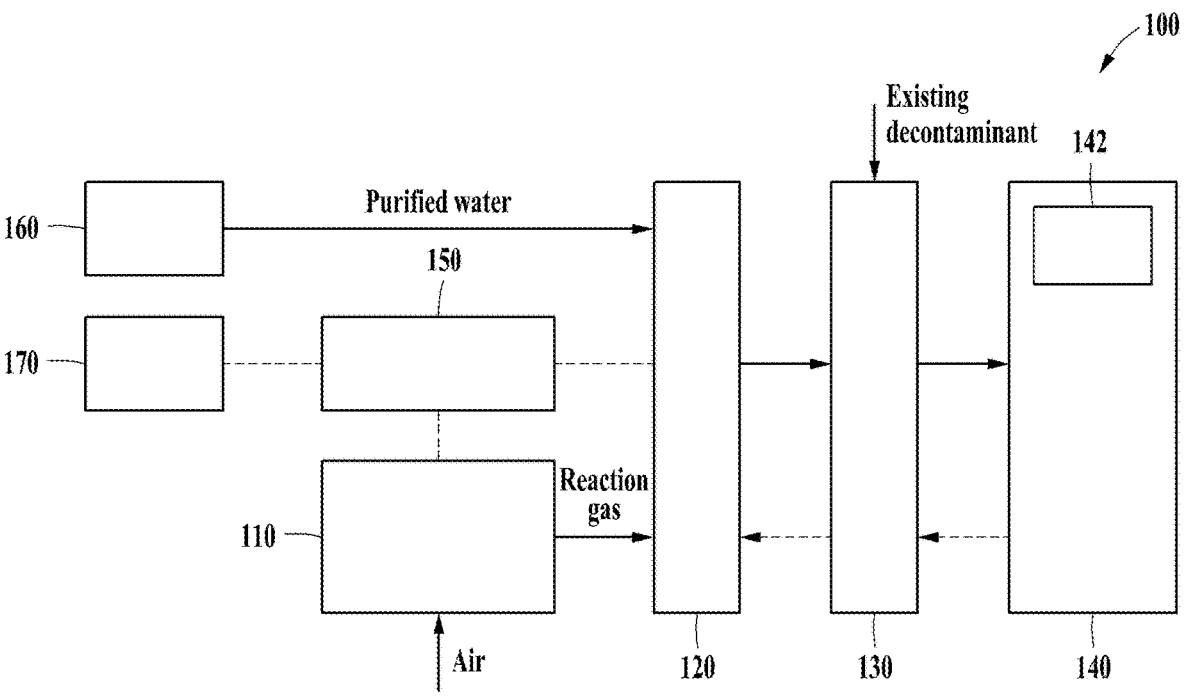
FIG. 1 is a block diagram schematically illustrating a decontaminant generating system according to an embodiment of the present disclosure.

Hereinafter, embodiments will be described in detail with reference to the accompanying drawings. However, various alterations and modifications may be made to the embodiments. Here, the embodiments are not construed as limited to the disclosure. The embodiments should be understood to include all changes, equivalents, and replacements within the idea and the technical scope of the disclosure.

The terminology used herein is for the purpose of describing particular embodiments only and is not to be limiting of the embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which the embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the embodiments with reference to the accompanying drawings, like reference numerals refer to like components and a repeated description related thereto will be omitted. In the description of embodiments, detailed description of well-known related structures or functions will be omitted when it is deemed that such description will cause ambiguous interpretation of the present disclosure.

In addition, terms such as first, second, A, B, (a), (b), and the like may be used to describe components of the embodiments. These terms are used only for the purpose of discriminating one component from another component, and the nature, the sequences, or the orders of the components are not limited by the terms.

The same name may be used to describe an element included in the embodiments described above and an element having a common function. Unless otherwise mentioned, the descriptions on the embodiments may be applicable to the following embodiments and thus, duplicated descriptions will be omitted for conciseness.

A decontaminant generating system includes an active species generation unit configured to generate an active species for decontamination, a gas-liquid mixing unit configured to form reaction activated water by dissolving the active species for decontamination generated from the active species generation unit in an aqueous solution, a decontaminant mixing unit configured to form a decontaminant by mixing the reaction activated water formed in the gas-liquid mixing unit with a decontamination composition in a granular form, a powder form, or both forms, a storage configured to store the decontaminant formed in the decontaminant mixing unit, a spraying unit configured to spray the decontaminant stored in the storage, and an integrated control unit configured to control operating variables and perform monitoring in real time.

The decontaminant generating system may purify a local water source, generate reaction activated water by mixing the purified water with the active species for decontamination generated using the active species generation unit, and, if necessary, mix the reaction activated water with an existing decontaminant to be stored stably by securing decontamination performance.

FIG. 1 is a block diagram schematically illustrating a decontaminant generating system according to an embodiment of the present disclosure.

Referring to FIG. 1, a decontaminant generating system 100 according to an embodiment of the present disclosure includes an active species generation unit 110, a gas-liquid mixing unit 120, a decontaminant mixing unit 130, a storage 140, a spraying unit 142, an integrated control unit 150, a water purification unit 160, and an integrated power unit 170.

The active species generation unit 110 generates active species for decontamination.

In an embodiment, the active species for decontamination may include at least one selected from the group consisting of an active nitrogen species, an active oxygen species, and effective chlorine. The type of active species refers to a chemical species capable of demonstrating decontamination performance.

The active nitrogen species may include at least one selected from the group consisting of $NO_3^-$, $NO_2^-$, and $ONOO^-$.

The active oxygen species may include at least one selected from the group consisting of $H_2O_2$, $O_3$, and $OH^-$.

The effective chlorine may include $Ca(ClO)_2$, $NaClO$, and $HClO^-$.

In an embodiment, the active species generation unit 110 may receive external air without additional supply of an external discharge gas, and generate the active species for decontamination through discharge of atmospheric pressure plasma by applying a frequency to the supplied external air.

The frequency may be in a range of 10 kHz to 2.45 GHz, 10 kHz to 2 GHz, 10 kHz to 1.5 GHz, 10 kHz to 1 GHz, 100 kHz to 2.45 GHz, 100 kHz to 2 GHz, 100 kHz to 1.5 GHz, 100 kHz to 1 GHz, 1 GHz to 2.45 GHz, 1 GHz to 2 GHz, or 1 GHz to 1.5 GHz.

In an embodiment, the active species generation unit 110 may the active species generation unit may include at least one selected from the group consisting of a plasma discharge module, an electrolysis module, a photochemical production module, a high energy beam, and a nano-catalyst module.

For example, as a method of utilizing plasma discharge, an electrode structure capable of causing an air or underwater discharge in an atmosphere or underwater without a supply gas may be designed so that plasma is discharged in the designed electrode structure, and active species for decontamination generated by the plasma discharge may be dissolved in an aqueous solution to provide reaction activated water. An active species that may be generated by utilizing oxygen, nitrogen, and water in the atmosphere may be largely divided into the active oxygen species and the active nitrogen species. In particular, ionized active species may decompose an organic material and sterilize various bacteria.

In an embodiment, the active species generation unit 110 may generate an active species for decontamination having a concentration of 1 wt % to 10 wt %, 1 wt % to 8 wt %, 1 wt % to 5 wt %, 1 wt % to 3 wt %, 3 wt % to 10 wt %, 3 wt % to 8 wt %, 3 wt % to 5 wt %, 5 wt % to 10 wt %, 5 wt % to 8 wt %, or 8 wt % to 10 wt %.

In an embodiment, the active species for decontamination may be generated at a production speed of 10 L/h to 1,000 L/h, 10 L/h to 800 L/h, 10 L/h to 500 L/h, 10 L/h to 300 L/h, 10 L/h to 100 L/h, 100 L/h to 1,000 L/h, 100 L/h to 800 L/h, 100 L/h to 500 L/h, 100 L/h to 300 L/h, 300 L/h to 1,000 L/h, 300 L/h to 800 L/h, 300 L/h to 500 L/h, 500 L/h to 1,000 L/h, 500 L/h to 800 L/h, or 800 L/h to 1,000 L/h by the active species generation unit 110.

According to an embodiment of the present disclosure, the active species for decontamination may be generated by the following process. Water supplied to the water purification unit 160 may be produced as an active species with a high concentration by the gas-liquid mixing unit 120 through the active species generation unit 110, and may be transferred to the storage 140 through the decontaminant mixing unit 130 together with an existing decontaminant selectively, if necessary. The transferred active species for decontamination may be used for decontamination through the spraying unit 142.

The gas-liquid mixing unit 120 forms a reaction activated water by dissolving the active species for decontamination generated from the active species generation unit 110 in an aqueous solution.

In an embodiment, the gas-liquid mixing unit 120 is a device for dissolving the active species for decontamination having a high concentration generated from the active species generation unit 110 in an aqueous solution with high efficiency and may include a packed column, a module type membrane contactor, or both.

In an embodiment, the gas-liquid mixing unit 120 may dissolve 99% or more of a high-concentration gas.

The decontaminant mixing unit 130 may form a decontaminant by mixing the reaction activated water formed in the gas-liquid mixing unit 120 with a decontamination composition in a granular form, a powder form, or both forms.

In an embodiment, the decontamination composition in a granular form, a powder form, or both forms may provide a decontamination reaction tailored to a decontamination target.

The decontamination composition in a granular form, a powder form, or both forms may include at least one selected from the group consisting of a commercial decontaminant, a chlorine-based decontaminant, and an oxygen-based decontaminant.

For example, a commercially available water-soluble decontaminant (chlorine-based) or a decontamination composition in a granular/powder form may be mixed by using a stirring device that uses a chemically resistant material for an existing decontaminant.

The storage 140 stores the decontaminant formed in the decontaminant mixing unit 130.

In an embodiment, the storage 140 may store the active species for decontamination for 7 to 30 days.

The storage 140 may block light in a state of maintaining predetermined temperature and pressure and use a material with high chemical resistance.

The storage 140 may further include a decontaminant characteristic diagnosis unit (not shown) for verifying the generated decontaminant. The decontaminant characteristic diagnosis unit may verify a pH, electrical conductivity, active species type, concentration, and the like with a DB of physical properties of the reaction activated water according to generation conditions.

The spraying unit 142 sprays the decontaminant stored in the storage 140.

In an embodiment, the decontaminant may decontaminate/sterilize chemical weapons and biological weapons that have penetrated 10 mm or more into a surface of a nonporous medium and a porous medium.

The integrated control unit 150 is provided to control operating variables and perform monitoring in real time.

In an embodiment, the integrated control unit 150 may integrally control the active species for decontamination to control a concentration and a production speed of the active species for decontamination.

Specifically, the integrated control unit 150 may be configured to control the operation of generating a decontaminant performed by the active species generation unit 110, the gas-liquid mixing unit 120, the decontaminant mixing unit 130, the storage 140, the spraying unit 142, the integrated control unit 150, the water purification unit 160, and the integrated power unit 170. The integrated control unit 150 may include a tablet personal computer (PC) or a PC controller, control software including a data acquisition (DAQ) system, a user-friendly control environment graphical user interface (GUI), and the like, and may include two GUI modes, including an engineer mode that enables precise control and confirmation of the decontaminant characteristics and an easy and simple operator mode. In particular, it may enable integrated control of the device in an activated water production module.

In an embodiment, the decontaminant generating system may further include the water purification unit 160, a cooling unit (not shown), or both.

The water purification unit 160 may generate optimized reaction activated water by analyzing the efficiency of reaction activated water production according to a water source and utilizing a local water source. In particular, the water purification performance may be selected at a level that does not affect the generation of reactive activated water and the decontamination performance. The purification type may be selected depending on required purification performance. For example, water purification devices of ultrafiltration (UF), nanofiltration (NF), reverse osmosis (RO), and ion exchange may be included, and the purification state may be monitored.

In an embodiment, the water purification unit 160 may control a contamination level of a water source obtained from the group consisting of tap water, river water, and sea water to an electrical conductivity of 1 mS/cm or less.

In an embodiment, the cooling unit may cool the decontaminant to a temperature range of 10° C. to 40° C.

The integrated power unit 170 is for power supply, and a power supply device may include a module that may supply a direct current (DC) and an alternating current (AC) and generate a high-frequency AC.

The decontaminant generating system according to an embodiment of the present disclosure may be operated in a fixed or movable manner. For movable use, the decontaminant generating system may have a size to fit into a standard container (e.g., 10 ft or 20 ft ISO standard container) to be unloaded and installed on site.

The type of active species for decontamination of the decontaminant may be controlled through the decontaminant generating system according to an embodiment of the present disclosure. In addition, the decontaminant may be generated in real time when a concentration, a generated amount, activity, and a production speed of the decontaminant are controlled. Also, the discharge of atmospheric pressure plasma is possible without additional supply of an external discharge gas. In addition, a decontamination reaction tailored to a decontamination target may be provided by mixing the decontaminant generated through the decontaminant generating system with a commercial decontaminant.

Chemical weapons (chemical agents) and biological weapons (biological agents) in a nonporous medium may be decontaminated/sterilized through the decontaminant generating system according to an embodiment of the present disclosure.

The decontaminant generating system according to an embodiment of the present disclosure may be applied to various decontamination and sterilization technologies including material property changes, surface modification, material synthesis, and cleaning in an environmental purification technology, a medical and bio-industry technology, an energy and material industry, a processing industry, and a weapon system.

Hereinafter, the present disclosure will be described in detail with reference to the following examples and comparative examples. However, the technical idea of the present disclosure is not limited or restricted thereto.

Examples

In this example, reactive activated water was produced using microwave plasma, water, and air to decontaminate toxic chemicals and sterilize toxic biological substances.

In the present disclosure, when comparing a new substance treated as a toxic chemical substance with 10% hydrogen peroxide, a test of removal by using two types of reaction activated water was performed, and a decrease in area of a corresponding peak was observed over time using GC.

Figure 2:
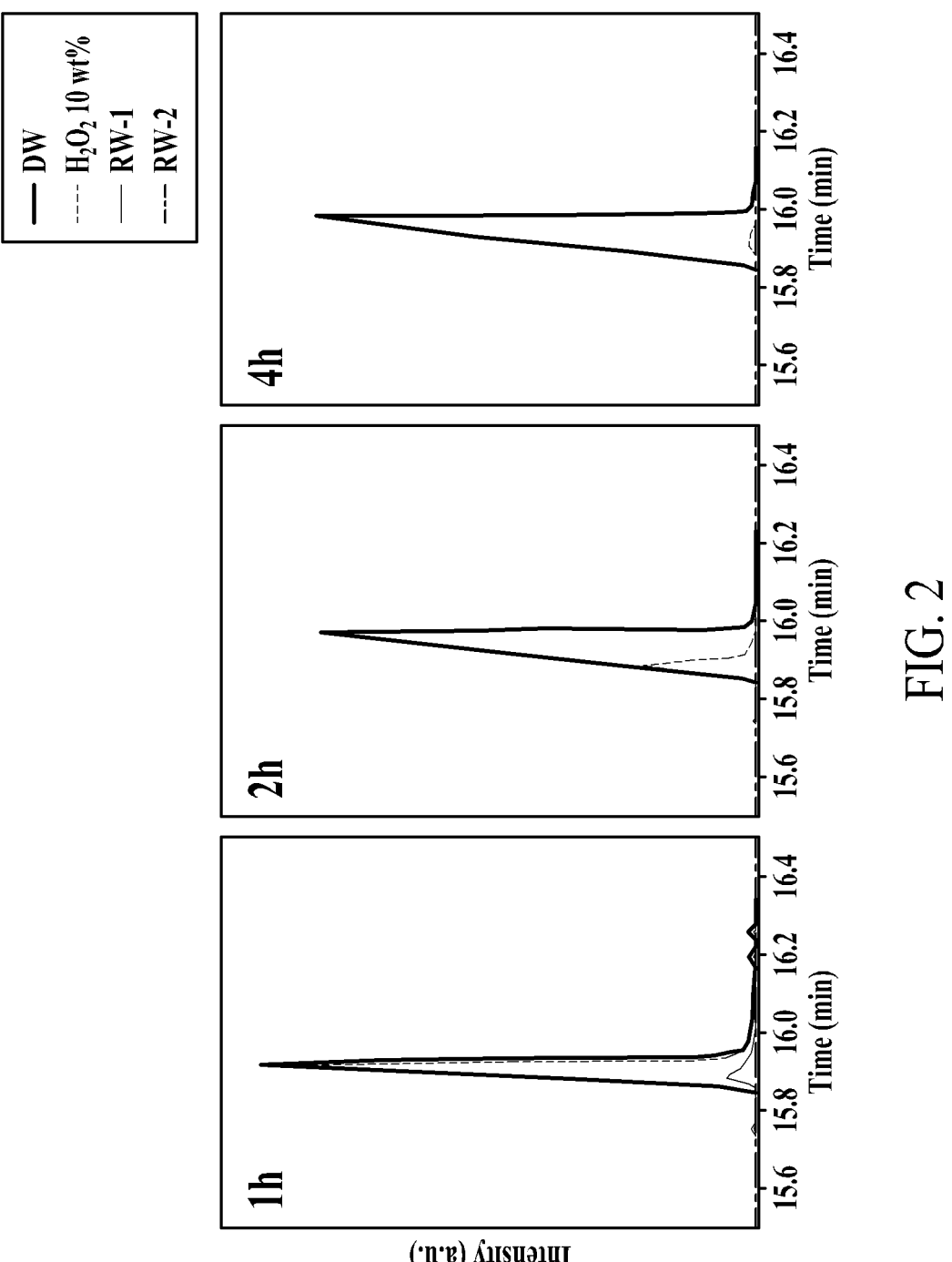
FIG. 2 illustrates graphs of results of decomposing an organic material using a decontaminant generated in a decontaminant generating system according to an embodiment of the present disclosure.
Figure 3:
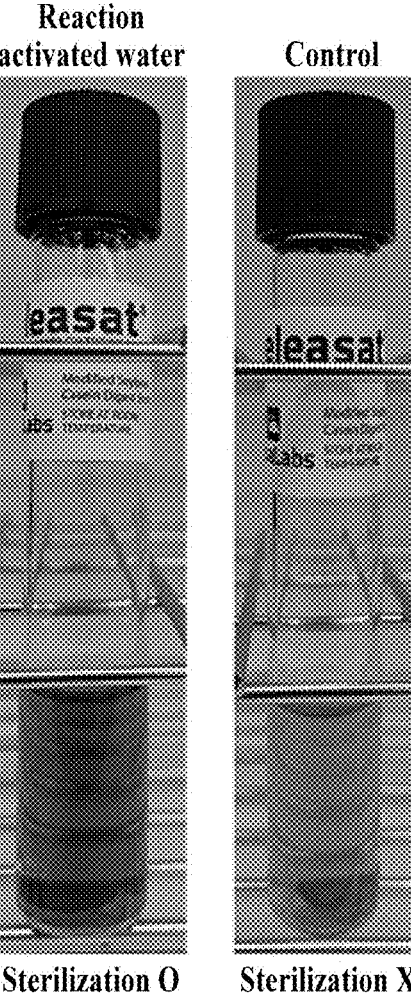
FIG. 3 illustrates images of results of sterilization of biological spores using a decontaminant generated in a decontaminant generating system according to an embodiment of the present disclosure.

FIG. 2 illustrates graphs of results of decomposing an organic material using a decontaminant generated in a decontaminant generating system according to an embodiment of the present disclosure, and FIG. 3 illustrates images of results of sterilization of biological spores using a decontaminant generated in a decontaminant generating system according to an embodiment of the present disclosure.

Referring to FIGS. 2 and 3, in the present disclosure, a test was performed to remove gram-positive bacterial spores using reaction activated water, and it was confirmed that spores exposed for a certain period of time were sterilized and died without growing in a medium.

Figure 4:
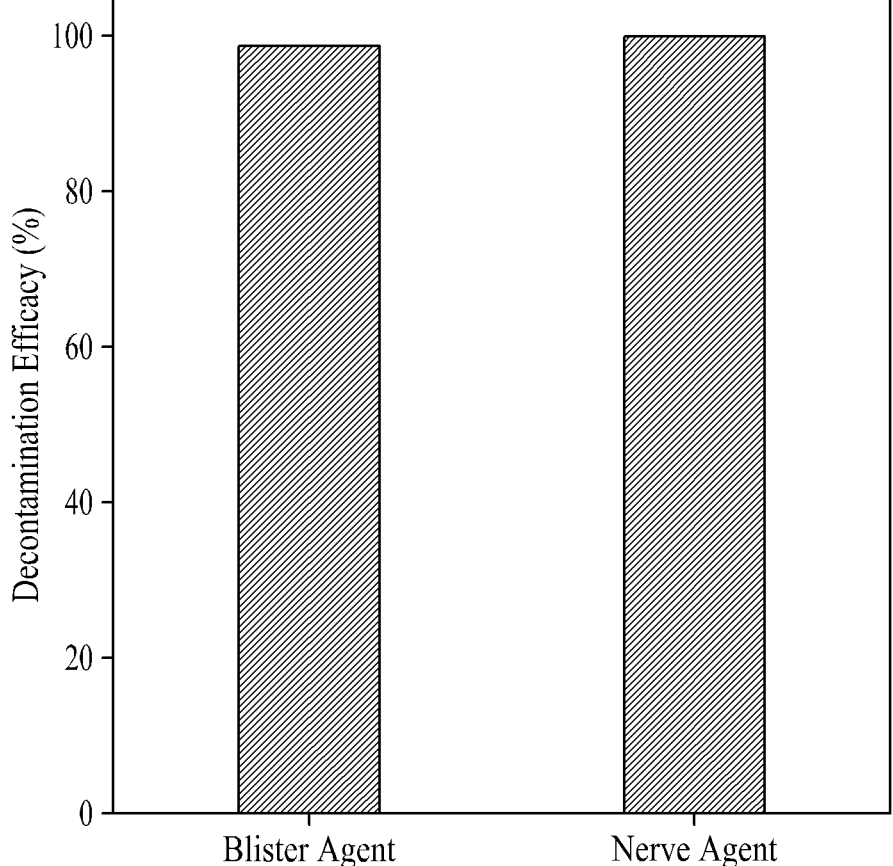
FIG. 4 illustrates a graph showing decontamination effects of a blister agent and a nerve agent using a decontaminant generated in a decontaminant generating system according to an embodiment of the present disclosure.

FIG. 4 illustrates a graph showing decontamination effects of a blister agent and a nerve agent using a decontaminant generated in a decontaminant generating system according to an embodiment of the present disclosure.

Referring to FIG. 4, it was confirmed that the decontaminant (the reaction activated water) of the present disclosure exhibited a great decontamination effect against traditional agents such as the nerve agent and the blister agent.

Figure 5:
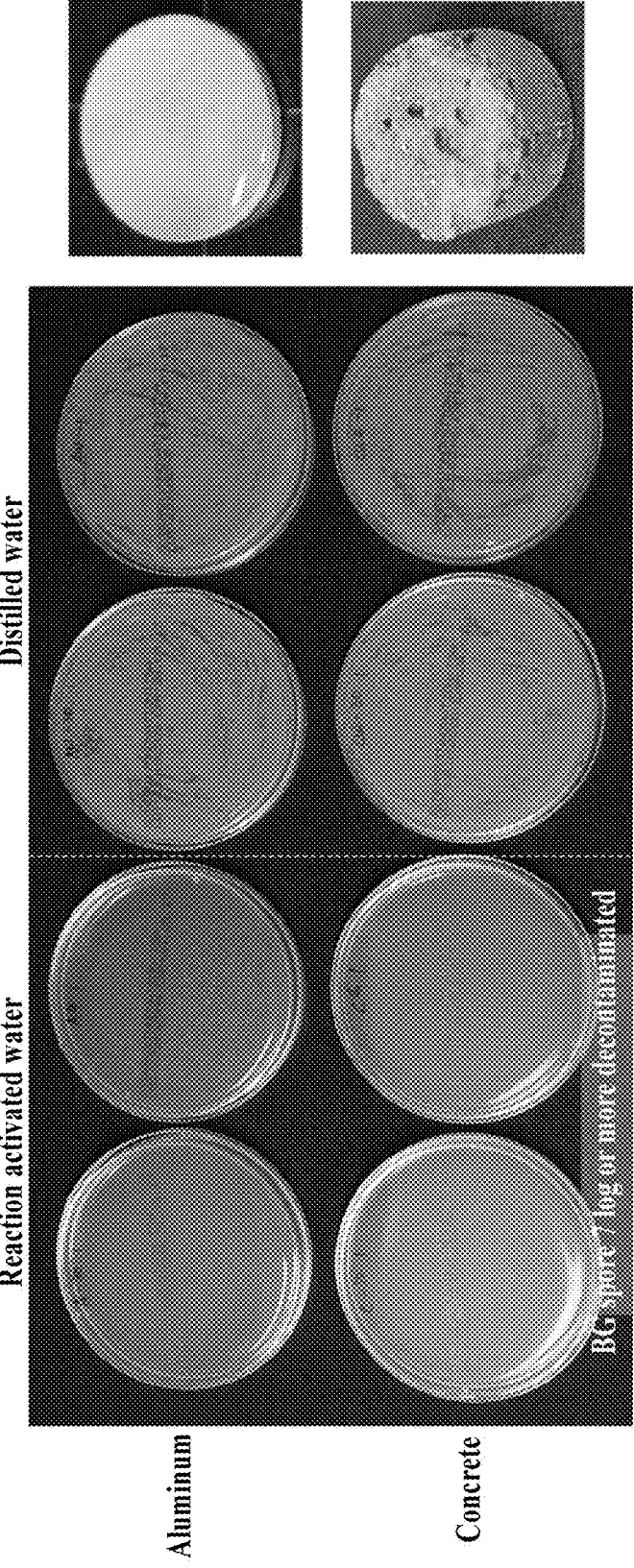
FIG. 5 illustrates images of results of sterilization of biological spores using a decontaminant generated in a decontaminant generating system according to an embodiment of the present disclosure.

FIG. 5 illustrates images of results of sterilization of biological spores using a decontaminant generated in a decontaminant generating system according to an embodiment of the present disclosure.

As shown in FIG. 5, it was confirmed that the decontaminant (the reaction activated water) of the present disclosure exhibited a great effect in decontaminating biological spores in nonporous and porous media.

While the embodiments are described with reference to drawings, it will be apparent to one of ordinary skill in the art that various alterations and modifications in form and details may be made in these embodiments without departing from the spirit and scope of the claims and their equivalents. For example, suitable results may be achieved if the described techniques are performed in a different order, and/or if components in a described system, architecture, device, or circuit are combined in a different manner, or replaced or supplemented by other components or their equivalents.

Therefore, other implementations, other embodiments, and equivalents to the claims are also within the scope of the following claims.

What is claimed is:

1. A decontaminant generating system comprising:
    an active species generation unit configured to generate an active species for decontamination;
    wherein the active species generation unit is configured to:
       receive external air without additional supply of an external discharge gas; and
       generate the active species for decontamination through discharge of atmospheric pressure plasma by applying a frequency of 10 kHz to 2.45 GHz to the supplied external air,
    a gas-liquid mixing unit configured to form reaction activated water by dissolving the active species for decontamination generated from the active species generation unit in an aqueous solution;
    a decontaminant mixing unit configured to form a decontaminant by mixing the reaction activated water formed in the gas-liquid mixing unit with a decontamination composition in a granular form, a powder form, or both forms;
    a storage configured to store the decontaminant formed in the decontaminant mixing unit, wherein the storage is configured to block light and maintain a predetermined temperature and pressure of the formed decontaminant;
    wherein the storage comprises a decontaminant characteristic diagnosis unit configured to verify a pH, electrical conductivity, active species type, or concentration of the decontaminant;
    a spraying unit configured to spray the decontaminant stored in the storage;
    an integrated control unit configured to configured to integrally control the active species for decontamination to control a concentration and a production speed of the active species for decontamination;
    a water purification unit configured to control a contamination level of a water source obtained from the group consisting of tap water, river water, and sea water to an electrical conductivity of 1 mS/cm or less; and
    a cooling unit configured to cool the decontaminant to a temperature range of 10° C. to 40° C.

* * * * *